US010137243B2

(12) United States Patent
Wang et al.

(10) Patent No.: US 10,137,243 B2
(45) Date of Patent: Nov. 27, 2018

(54) INFUSION DEVICES WITH DISTRIBUTED MOTOR CONTROL AND RELATED OPERATING METHODS

(71) Applicant: MEDTRONIC MINIMED, INC., Northridge, CA (US)

(72) Inventors: Yongbo Wang, Arcadia, CA (US); Steve Chow, Northridge, CA (US); David P. Lewinski, Westlake Village, CA (US); Linda I. Torres, Moorpark, CA (US); Alexander S. Campbell, Tarzana, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 553 days.

(21) Appl. No.: 14/721,800

(22) Filed: May 26, 2015

(65) Prior Publication Data
US 2016/0346458 A1   Dec. 1, 2016

(51) Int. Cl.
*A61M 5/145* (2006.01)
*G16H 40/40* (2018.01)
(Continued)

(52) U.S. Cl.
CPC ........ *A61M 5/145* (2013.01); *A61M 5/16877* (2013.01); *A61M 5/172* (2013.01);
(Continued)

(58) Field of Classification Search
CPC .............. A61M 5/145; A61M 5/16831; A61M 5/1452; A61M 2005/14208;
(Continued)

(56) References Cited

U.S. PATENT DOCUMENTS

| 3,631,847 A | 1/1972 | Hobbs, II |
| 4,212,738 A | 7/1980 | Henne |

(Continued)

FOREIGN PATENT DOCUMENTS

| DE | 4329229 | 3/1995 |
| EP | 0319268 | 11/1988 |

(Continued)

OTHER PUBLICATIONS

PCT Search Report (PCT/US02/03299), dated Oct. 31, 2002, Medtronic Minimed, Inc.
(Continued)

*Primary Examiner* — Lauren P Farrar
(74) *Attorney, Agent, or Firm* — Lorenz & Kopf, LLP

(57) ABSTRACT

Infusion systems, infusion devices, and related operating methods are provided. An exemplary infusion device includes a motor operable to deliver fluid to a body of a user, a first control module, and a second control module. The first control module and the second control module are coupled to one another. The first control module enables input power for the motor in accordance with a handshaking sequence of communications between the first control module and the second control module and provides a dosage command to the second control module, with the second control module operating the motor using the input power based on the dosage command in accordance with the handshaking sequence of communications.

17 Claims, 7 Drawing Sheets

US 10,137,243 B2

Page 2

(51) Int. Cl.
*A61M 5/168* (2006.01)
*A61M 5/172* (2006.01)
*A61M 5/142* (2006.01)

(52) U.S. Cl.
CPC ... *G16H 40/40* (2018.01); *A61M 2005/14208* (2013.01); *A61M 2005/14506* (2013.01); *A61M 2205/50* (2013.01); *A61M 2205/502* (2013.01); *A61M 2205/52* (2013.01); *A61M 2230/201* (2013.01)

(58) Field of Classification Search
CPC .. A61M 2205/6018; A61M 2205/3569; A61M 5/16877; A61M 5/172; A61M 2230/201; A61M 2205/52; A61M 2205/50; A61M 2205/502; A61M 2005/14506; G06F 19/3468; G16H 40/40
See application file for complete search history.

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |

(56) References Cited

U.S. PATENT DOCUMENTS

| | | | |
|---|---|---|---|
| 6,162,611 A | 12/2000 | Heller et al. | |
| 6,175,752 B1 | 1/2001 | Say et al. | |
| 6,183,412 B1* | 2/2001 | Benkowski | A61M 1/1031 600/16 |
| 6,246,992 B1 | 6/2001 | Brown | |
| 6,248,093 B1 | 6/2001 | Moberg | |
| 6,259,937 B1 | 7/2001 | Schulman et al. | |
| 6,329,161 B1 | 12/2001 | Heller et al. | |
| 6,408,330 B1 | 6/2002 | DeLaHuerga | |
| 6,424,847 B1 | 7/2002 | Mastrototaro et al. | |
| 6,472,122 B1 | 10/2002 | Schulman et al. | |
| 6,484,045 B1 | 11/2002 | Holker et al. | |
| 6,484,046 B1 | 11/2002 | Say et al. | |
| 6,485,465 B2 | 11/2002 | Moberg et al. | |
| 6,503,381 B1 | 1/2003 | Gotoh et al. | |
| 6,514,718 B2 | 2/2003 | Heller et al. | |
| 6,544,173 B2 | 4/2003 | West et al. | |
| 6,553,263 B1 | 4/2003 | Meadows et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,560,741 B1 | 5/2003 | Gerety et al. | |
| 6,565,509 B1 | 5/2003 | Say et al. | |
| 6,579,690 B1 | 6/2003 | Bonnecaze et al. | |
| 6,589,229 B1 | 7/2003 | Connelly et al. | |
| 6,591,125 B1 | 7/2003 | Buse et al. | |
| 6,592,745 B1 | 7/2003 | Feldman et al. | |
| 6,605,200 B1 | 8/2003 | Mao et al. | |
| 6,605,201 B1 | 8/2003 | Mao et al. | |
| 6,607,658 B1 | 8/2003 | Heller et al. | |
| 6,616,819 B1 | 9/2003 | Liamos et al. | |
| 6,618,934 B1 | 9/2003 | Feldman et al. | |
| 6,623,501 B2 | 9/2003 | Heller et al. | |
| 6,641,533 B2 | 11/2003 | Causey, III et al. | |
| 6,654,625 B1 | 11/2003 | Say et al. | |
| 6,659,980 B2 | 12/2003 | Moberg et al. | |
| 6,671,554 B2 | 12/2003 | Gibson et al. | |
| 6,676,816 B2 | 1/2004 | Mao et al. | |
| 6,689,265 B2 | 2/2004 | Heller et al. | |
| 6,728,576 B2 | 4/2004 | Thompson et al. | |
| 6,733,471 B1 | 5/2004 | Ericson et al. | |
| 6,740,072 B2 | 5/2004 | Starkweather et al. | |
| 6,746,582 B2 | 6/2004 | Heller et al. | |
| 6,747,556 B2 | 6/2004 | Medema et al. | |
| 6,749,740 B2 | 6/2004 | Liamos et al. | |
| 6,752,787 B1 | 6/2004 | Causey, III et al. | |
| 6,809,653 B1 | 10/2004 | Mann et al. | |
| 6,817,990 B2 | 11/2004 | Yap et al. | |
| 6,827,702 B2 | 12/2004 | Lebel et al. | |
| 6,881,551 B2 | 4/2005 | Heller et al. | |
| 6,892,085 B2 | 5/2005 | McIvor et al. | |
| 6,893,545 B2 | 5/2005 | Gotoh et al. | |
| 6,895,263 B2 | 5/2005 | Shin et al. | |
| 6,916,159 B2 | 7/2005 | Rush et al. | |
| 6,932,584 B2 | 8/2005 | Gray et al. | |
| 6,932,894 B2 | 8/2005 | Mao et al. | |
| 6,942,518 B2 | 9/2005 | Liamos et al. | |
| 7,153,263 B2 | 12/2006 | Carter et al. | |
| 7,153,289 B2 | 12/2006 | Vasko | |
| 7,323,142 B2 | 1/2008 | Pendo et al. | |
| 7,396,330 B2 | 7/2008 | Banet et al. | |
| 7,402,153 B2 | 7/2008 | Steil et al. | |
| 7,621,893 B2 | 11/2009 | Moberg et al. | |
| 8,474,332 B2 | 7/2013 | Bente, IV | |
| 8,523,803 B1 | 9/2013 | Favreau | |
| 8,603,026 B2 | 12/2013 | Favreau | |
| 8,603,027 B2 | 12/2013 | Favreau | |
| 8,674,288 B2 | 3/2014 | Hanson et al. | |
| 2001/0044731 A1 | 11/2001 | Coffman et al. | |
| 2002/0013518 A1* | 1/2002 | West | A61B 5/1113 600/300 |
| 2002/0055857 A1 | 5/2002 | Mault et al. | |
| 2002/0082665 A1 | 6/2002 | Haller et al. | |
| 2002/0137997 A1 | 9/2002 | Mastrototaro et al. | |
| 2002/0161288 A1 | 10/2002 | Shin et al. | |
| 2003/0060765 A1 | 3/2003 | Campbell et al. | |
| 2003/0078560 A1 | 4/2003 | Miller et al. | |
| 2003/0088166 A1 | 5/2003 | Say et al. | |
| 2003/0144581 A1 | 7/2003 | Conn et al. | |
| 2003/0152823 A1 | 8/2003 | Heller | |
| 2003/0176183 A1 | 9/2003 | Drucker et al. | |
| 2003/0188427 A1 | 10/2003 | Say et al. | |
| 2003/0199744 A1 | 10/2003 | Buse et al. | |
| 2003/0208113 A1 | 11/2003 | Mault et al. | |
| 2003/0220552 A1 | 11/2003 | Reghabi et al. | |
| 2004/0061232 A1 | 4/2004 | Shah et al. | |
| 2004/0061234 A1 | 4/2004 | Shah et al. | |
| 2004/0064133 A1 | 4/2004 | Miller et al. | |
| 2004/0064156 A1 | 4/2004 | Shah et al. | |
| 2004/0073095 A1 | 4/2004 | Causey, III et al. | |
| 2004/0074785 A1 | 4/2004 | Holker et al. | |
| 2004/0093167 A1 | 5/2004 | Braig et al. | |
| 2004/0097796 A1 | 5/2004 | Berman et al. | |
| 2004/0102683 A1 | 5/2004 | Khanuja et al. | |
| 2004/0111017 A1 | 6/2004 | Say et al. | |
| 2004/0122353 A1 | 6/2004 | Shahmirian et al. | |
| 2004/0167465 A1 | 8/2004 | Mihai et al. | |
| 2004/0263354 A1 | 12/2004 | Mann et al. | |
| 2005/0038331 A1 | 2/2005 | Silaski et al. | |
| 2005/0038680 A1 | 2/2005 | McMahon et al. | |
| 2005/0154271 A1 | 7/2005 | Rasdal et al. | |
| 2005/0192557 A1 | 9/2005 | Brauker et al. | |
| 2006/0173444 A1 | 8/2006 | Choy et al. | |
| 2006/0184154 A1 | 8/2006 | Moberg et al. | |
| 2006/0229694 A1 | 10/2006 | Schulman et al. | |
| 2006/0238333 A1 | 10/2006 | Welch et al. | |
| 2006/0293571 A1 | 12/2006 | Bao et al. | |
| 2007/0088521 A1 | 4/2007 | Shmueli et al. | |
| 2007/0135866 A1 | 6/2007 | Baker et al. | |
| 2008/0154503 A1 | 6/2008 | Wittenber et al. | |
| 2009/0081951 A1 | 3/2009 | Erdmann et al. | |
| 2009/0082635 A1 | 3/2009 | Baldus et al. | |
| 2013/0253420 A1* | 9/2013 | Favreau | F04B 49/10 604/67 |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

(56) References Cited

OTHER PUBLICATIONS

Brackenridge B P (1992). Carbohydrate Gram Counting A Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting A Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.

(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.

(56) References Cited

OTHER PUBLICATIONS

Monroe, D., "Novel Implantable Glucose Sensors," ACL, Dec. 1989, pp. 8-16.

Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.

Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.

Nakamoto, S., et al., "A Lift-Off Method for Patterning Enzyme-Immobilized Membranes in Multi-Biosensors," Sensors and Actuators 13, 1988, pp. 165-172.

Nishida, Kenro, et al., "Clinical applications of teh wearable artifical endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designd biocompatible membrane, 2-methacryloyloxyethylphosphorylcholine-co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Disaccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G. et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

* cited by examiner

INFUSION DEVICES WITH DISTRIBUTED MOTOR CONTROL AND RELATED OPERATING METHODS

TECHNICAL FIELD

Embodiments of the subject matter described herein relate generally to medical devices, and more particularly, embodiments of the subject matter relate to fluid infusion devices with distributed motor control.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Continuous insulin infusion provides greater control of a diabetic's condition, and hence, control schemes have been developed that allow insulin infusion pumps to monitor and regulate a user's blood glucose level in a substantially continuous and autonomous manner. For example, an insulin infusion pump may operate in a closed-loop operating mode overnight while a user is sleeping to regulate the user's glucose level to a target glucose level. However, care must be taken to avoid potentially compromising a user's condition and ensure compliance with applicable regulatory requirements in the event of software errors, hardware errors, or other unpredictable or anomalous operating conditions.

BRIEF SUMMARY

Infusion devices, systems and related methods of operation are provided. One exemplary infusion device includes a motor operable to deliver fluid to a body of a user, a first control module, and a second control module coupled to the first control module and the motor. The first control module enables input power for the motor in accordance with a handshaking sequence of communications between the first control module and the second control module and provides a dosage command to the second control module. The second control module operates the motor using the input power based at least in part on the dosage command in accordance with the handshaking sequence of communications.

In another embodiment, an infusion device includes a motor operable to deliver fluid to a body of a user, a driver module coupled to the motor, a first control module, and a second control module coupled to the driver module and the first control module. The first control module provides a delivery request, enables input power to the driver module in response to an acknowledgment of the delivery request, and provides a delivery message after enabling the input power. The second control module provides the acknowledgment to the first control module in response to the delivery request and operates the driver module to provide the input power to the motor based on the delivery message.

In yet another embodiment, a method of operating a motor of an infusion device. The method involves enabling, by a first control module of the infusion device, input power from an energy source to a driver module coupled between the energy source and the motor in accordance with a first sequence of communications between the first control module and a second control module of the infusion device. After enabling the input power, the second control module enables output power from the driver module to the motor in accordance with a second sequence of communications between the first control module and the second control module. After enabling the output power from the driver module, the driver module is operated to provide the input power to the motor in accordance with a third sequence of communications between the first control module and the second control module.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
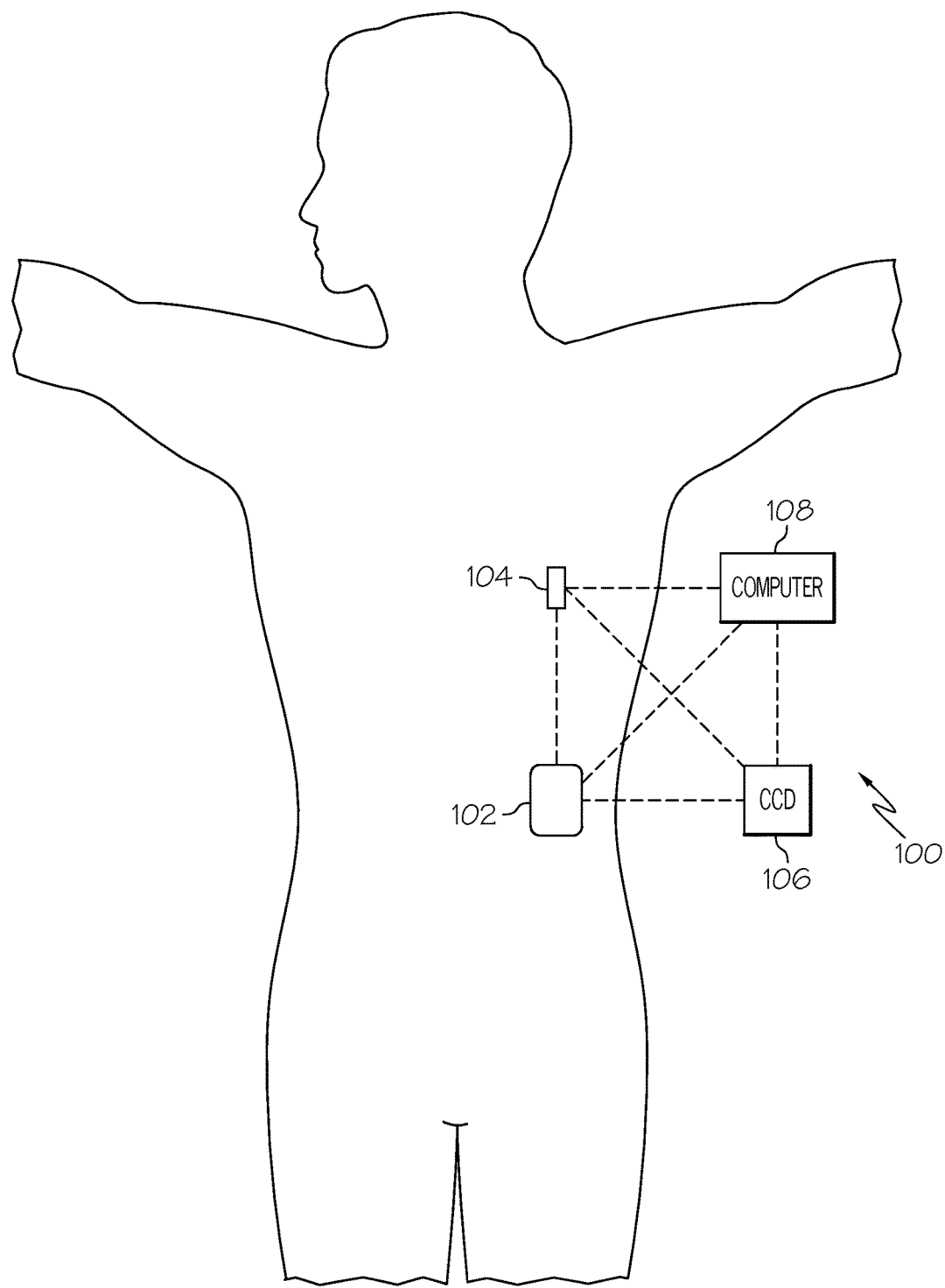
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device that includes a motor, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to fluid infusion devices including a motor that is operable to displace a plunger (or stopper) of a reservoir provided within the fluid infusion device to deliver a dosage of fluid, such as insulin, to the body of a user. The control of the motor is distributed across multiple control modules of the infusion device using handshaking communications sequences in a manner that reduces the likelihood of overdelivery or undetected underdelivery in the event of an error or anomalous condition with respect to one of the control modules. In this regard, either control module is capable of unilaterally disconnecting or otherwise disabling input power to the motor based on a failure to receive a communication from the other control module that is prescribed by the handshaking communications sequence within an applicable time limit, thereby mitigating the impact on fluid delivery that could otherwise result from an anomalous condition of the other control module. Additionally, either control module is capable of generating user notifications or alerts based on a failure to receive a communication from the other control module in accordance with the handshaking communications sequence, thereby immediately notifying a user of a potential anomalous condition with respect to the infusion device.

In one or more exemplary embodiments, a first control module of the infusion device enables input power from an energy source to a motor driver module coupled between the energy source and the motor in accordance with an initial setup sequence of communications between the first control module and a second control module of the infusion device. After the motor driver input power is enabled, the second control module enables the output power from the motor driver module to be input to the motor in accordance with a second setup sequence of communications between the first control module and the second control module. After the output power from the motor driver module has been enabled, the second control module operates the motor driver module in accordance with a dosage command received from the first control module. In this regard, the second control module operates the motor driver module to provide a predetermined portion of the input power corresponding to the dosage command from the energy source to the motor in accordance with a delivery sequence of communications between the first control module and the second control module. At any time during the delivery process, when either the first control module or the second control module fails to receive a communication from the other control module dictated by the applicable handshaking sequence, the respective control module may unilaterally disable electrical power from the energy source from being provided to the motor. In this manner, an anomalous condition does not result in overdelivery of fluid. Additionally, the respective control module may generate or otherwise provide an alert, so that a user may be immediately apprised of the potential anomalous condition. Thus, if the infusion device being operated in an autonomous delivery mode (e.g., a closed-loop operating mode), the user is notified when the autonomous delivery is interrupted so that the user may revert to manual monitoring and regulation of the user's physiological condition in a manner that prevents underdelivery of fluid that could otherwise result from terminating the autonomous operation of the infusion device.

FIG. 1 depicts one exemplary embodiment of an infusion system 100, which includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a physiological condition in the body of the user, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106 and/or the computer 108. In such embodiments, the sensing arrangement 104 may be configured to receive a biological sample, analyte, or the like, to measure a condition of the user.

As described above, in some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the patient's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402, 153, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid substantially continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example, only when the user is asleep or awake.

Figure 2:
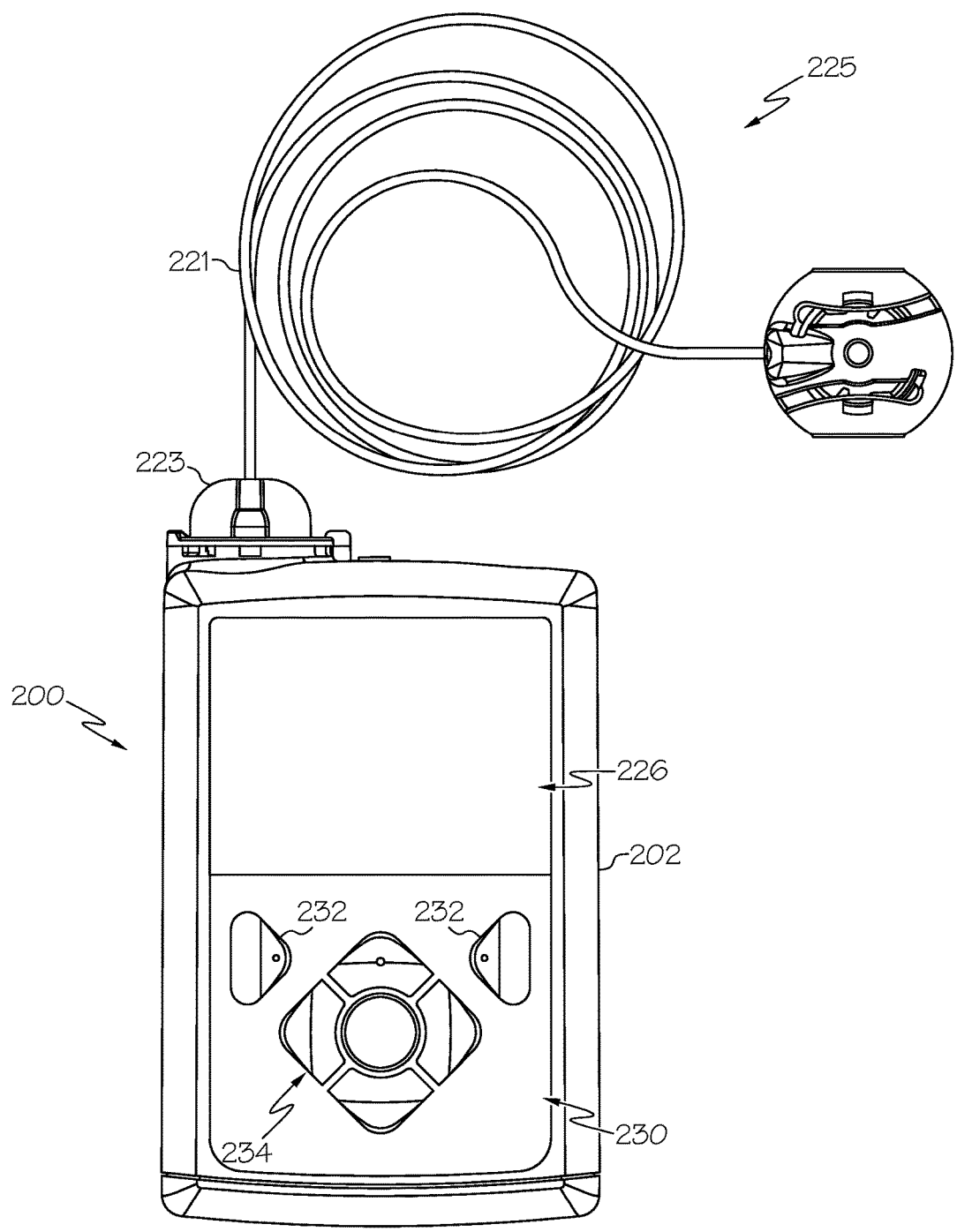
FIG. 2 depicts a plan view of an exemplary embodiment of a fluid infusion device suitable for use in the infusion system of FIG. 1.
Figure 3:
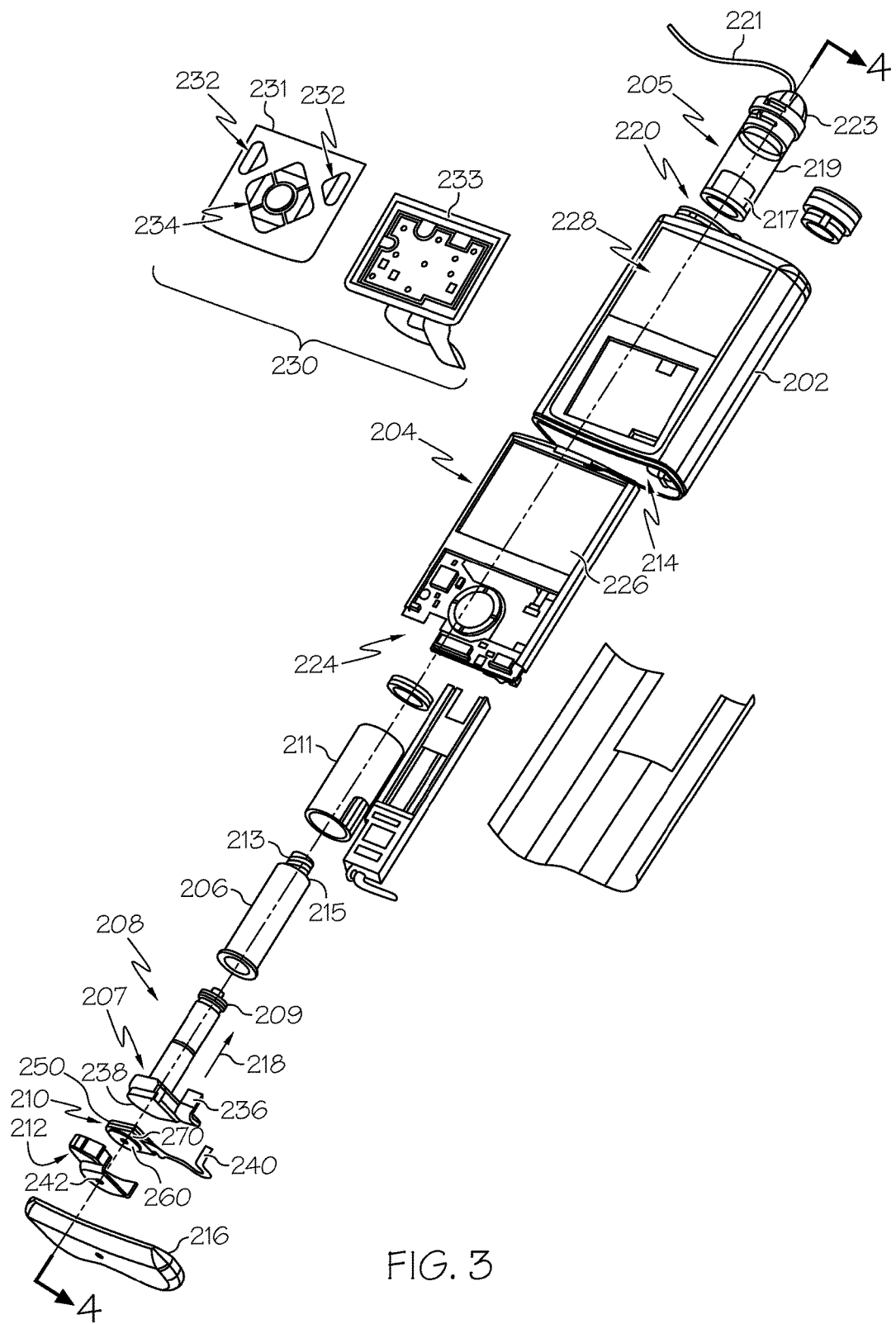
FIG. 3 is an exploded perspective view of the fluid infusion device of FIG. 2.
Figure 4:
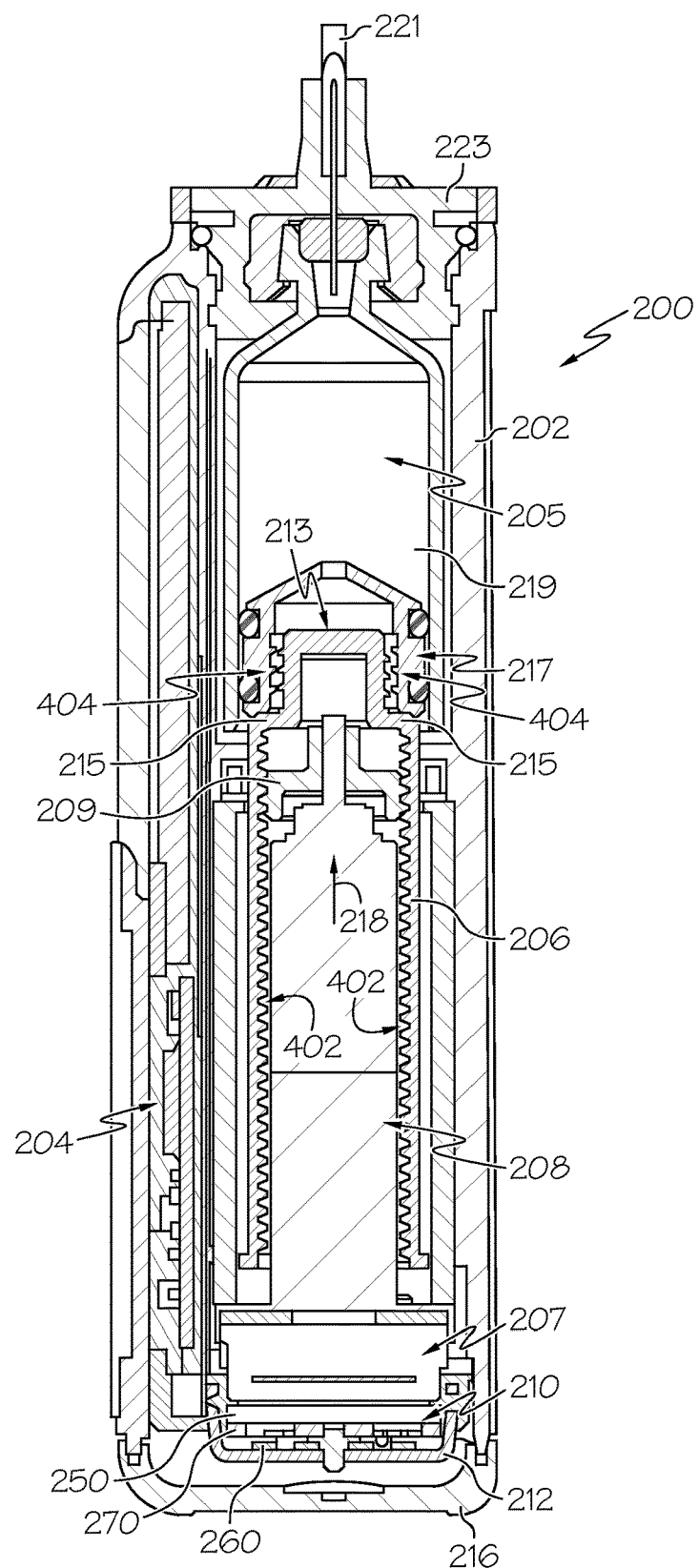
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a patient's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the patient's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
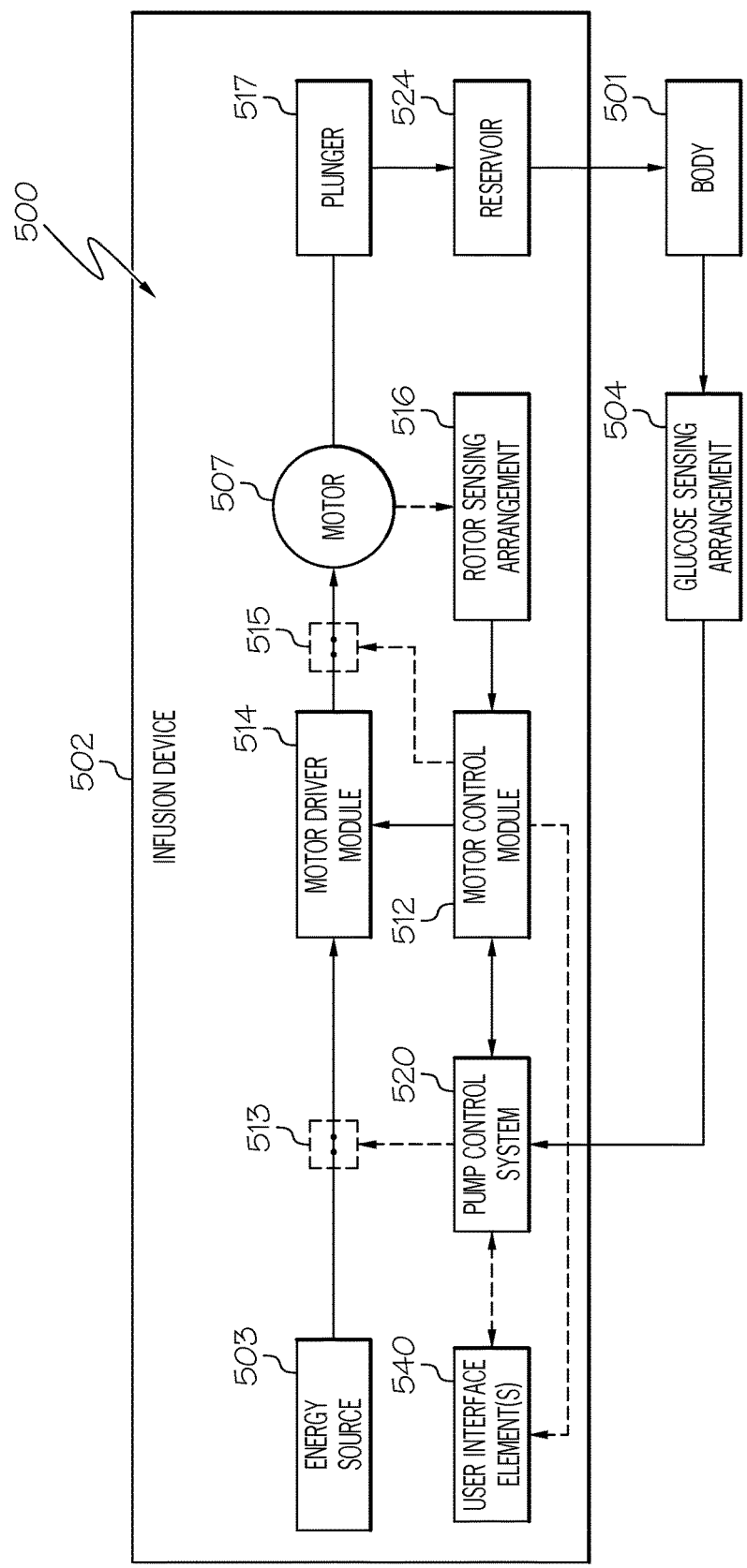
FIG. 5 is a block diagram of an exemplary control system suitable for use in a fluid infusion device, such as the fluid infusion device of FIG. 1 or FIG. 2.

FIG. 5 depicts an exemplary embodiment of a control system 500 suitable for use with an infusion device 502, such as the infusion device 102 in FIG. 1 or the infusion device 200 of FIG. 2. The control system 500 is configured to control or otherwise regulate a physiological condition in the body 501 of a user. In one or more exemplary embodiments, the condition being regulated is sensed, detected, measured or otherwise quantified by a sensing arrangement 504 (e.g., sensing arrangement 104) communicatively coupled to the infusion device 502. However, it should be noted that in alternative embodiments, the condition being regulated by the control system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the user's glucose level, which is being regulated in the body 501 of the user by the control system 500.

In exemplary embodiments, the sensing arrangement 504 includes one or more interstitial glucose sensing elements that generate or otherwise output electrical signals having a signal characteristic that is correlative to, influenced by, or otherwise indicative of the relative interstitial fluid glucose level in the body 501 of the user. The output electrical signals are filtered or otherwise processed to obtain a measurement value indicative of the user's interstitial fluid glucose level. A blood glucose meter, such as a finger stick device, may be utilized to directly sense, detect, measure or otherwise quantify the blood glucose in the body 501 of the user and output or otherwise provide a measured blood glucose value that may be utilized as a reference measurement for calibrating the sensing arrangement 504, and thereby converting a measurement value indicative of the user's interstitial fluid glucose level into a corresponding calibrated blood glucose measurement value. For purposes of explanation, sensor glucose value, sensed glucose value, glucose measurement value, or variants thereof should be understood to encompass any glucose value indicative of a current measured glucose level in the body of the user that is based on the electrical signals output by the sensing element(s) of the sensing arrangement 504.

The pump control module 520 generally represents the electronics and other components of the infusion device 502 that control operation of the fluid infusion device 502 according to a desired infusion delivery program in a manner that may be influenced by the sensed glucose value indicative of a current glucose level in the body 501 of the user. The particular operating mode being implemented by the pump control module 520 influences the generated dosage commands for operating the motor 507 to displace the plunger 517 within a fluid reservoir 524 and deliver insulin to the body 501 of the user. For example, in a closed-loop (CL) operating mode, the pump control module 520 generates or otherwise determines dosage commands for operating the motor 507 based on the difference between a sensed glucose value and the target (or commanded) glucose value to regulate the sensed glucose value to the target. In other operating modes, the pump control module 520 may generate or otherwise determine dosage commands configured to maintain the sensed glucose value below an upper glucose limit, above a lower glucose limit, or otherwise within a desired range of glucose values. In practice, the infusion device 502 may store or otherwise maintain the target glucose value and/or other glucose control value(s) in a data storage element accessible to the pump control module 520.

The target glucose value and other threshold values may be received from an external component (e.g., CCD 106 and/or computing device 108) or be input by a user via a user interface element 540 associated with the infusion device 502. In practice, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 540 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 5 depicts the user interface element(s) 540 as being integrated with the infusion device 502, in practice, one or more of the user interface element(s) 540 may be separate from the infusion device 502. The user interface element(s) 540 may be manipulated by the user to operate the infusion device 502 to deliver correction boluses, adjust target and/or threshold values, modify the delivery control scheme or operating mode, and the like, as desired. Additionally, one or more of the user interface element(s) 540 may be utilized by the pump control module 520 or the motor control module 512 to generate alerts or other user notifications.

Depending on the embodiment, the pump control module 520 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the pump control module 520, or in any practical combination thereof. In this regard, the pump control module 520 may include or otherwise access a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the pump control module 520. The computer-executable programming instructions, when read and executed by the pump control module 520, cause the pump control module 520 to determine dosage commands in accordance with a particular operating mode and perform various additional tasks, operations, functions, and processes described herein.

Still referring to FIG. 5, in the illustrated embodiment, the infusion device 502 also includes a motor control module 512 coupled to a motor 507 (e.g., motor assembly 207) via a motor driver module 514 coupled between an energy source 503 and the motor 507. The motor 507 is operable to displace a plunger 517 (e.g., plunger 217 via drive system 208) in a reservoir 524 (e.g., reservoir 205) and provide a desired amount of fluid to the body 501 of a user. In this regard, displacement of the plunger 517 results in the delivery of a fluid that is capable of influencing the condition in the body 501 of the user to the body 501 of the user via a fluid delivery path (e.g., via tubing 221 of an infusion set 225). The motor control module 512 is coupled to the motor driver module 514, and the motor control module 512 generates or otherwise provides command signals that operate the motor driver module 514 to provide power (or current) from the energy source 503 to the motor 507 to displace the plunger 517 in response to receiving, from the pump control module 520, a dosage command indicative of the desired amount of fluid to be delivered. The motor control module 512 is separate from the pump control module 520, and may similarly be implemented or realized with a general purpose processor, a microprocessor, a controller, a microcontroller, a state machine, an application specific integrated circuit, or the like. Steps of a method or algorithm described in connection with the embodiments disclosed herein may also be embodied directly in hardware, in firmware, in a software module executed by the motor control module 512, or in any practical combination thereof. In exemplary embodiments, the motor control module 512 includes or otherwise accesses a data storage element, which is capable of storing programming instructions for execution by the motor control module 512 to perform the tasks, operations, functions, and processes described herein.

In exemplary embodiments, the energy source 503 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 503 into alternating electrical signals applied to respective phases of the stator windings of the motor 507 that result in current flowing through the stator windings that generates a stator magnetic field and causes the rotor of the motor 507 to rotate.

The motor control module 512 is configured to receive or otherwise obtain a commanded dosage from the pump control module 520, convert the commanded dosage to a commanded translational displacement of the plunger 517, and command, signal, or otherwise operate the motor driver module 514 to cause the rotor of the motor 507 to rotate by an amount that produces the commanded translational displacement of the plunger 517. For example, the motor control module 512 may determine an amount of rotation of the rotor required to produce translational displacement of the plunger 517 that achieves the commanded dosage received from the pump control module 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 507 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 507 to achieve the desired delivery of fluid to the user.

In exemplary embodiments described herein, electrical power output from the energy source 503 is selectively provided to the input of the motor driver module 514 under control of the pump control module 520. For example, a switching arrangement 513 may be provided effectively electrically in series between the output of the energy source 503 (or a bus connected to the energy source 503) and the input to the motor driver module 514. In exemplary embodiments, the pump control module 520 operates the switching arrangement 513 to electrically disconnect the motor driver module 514 from the electrical power output by the energy source 503 (e.g., by opening or deactivating one or more switches) when the motor 507 is not being utilized to deliver fluid to the body 501 of the user. As described in greater detail below in the context of FIGS. 6-7, when the pump control module 520 determines it is desirable to operate the motor 507 to implement a dosage command, the pump control module 520 operates the switching arrangement 513 to electrically connect the energy source 503 and the motor driver module 514 to enable input electrical power to the motor driver module 514 from the energy source 503 in accordance with a handshaking sequence of communications with the motor control module 512.

Still referring to FIG. 5, in exemplary embodiments described herein, electrical power output from the motor driver module 514 is selectively provided to the input(s) of the motor 507 under control of the motor control module 512. For example, a second switching arrangement 515 may be provided effectively electrically in series between the output of the motor driver module 514 and the input(s) (e.g., the stator winding(s)) of the motor 507. Thus, the motor control module 512 may operate the switching arrangement 515 to electrically disconnect the motor 507 from the output of the motor driver module 514, thereby preventing power from being applied to the motor 507. In this regard, the switching arrangement 515 provides redundancy for disconnecting the motor 507 from the electrical power from the energy source 503. As described in greater detail below in the context of FIGS. 6-7, prior to operating the motor driver module 514 to implement a dosage command, the motor control module 512 operates the switching arrangement 515 to electrically connect the output of the motor driver module 514 to the motor 507 to enable electrical power being applied to the motor 507 in accordance with a second handshaking sequence of communications with the pump control module 520.

It should be appreciated that FIG. 5 is a simplified representation of the infusion device 502 for purposes of explanation and is not intended to limit the subject matter described herein in any way. In this regard, depending on the embodiment, the features and/or functionality of the switching arrangement 513 may be implemented by or otherwise integrated into the energy source 503 or the motor driver module 514. Similarly, the features and/or functionality of the switching arrangement 515 may be implemented by or otherwise integrated into the motor driver module 514 or the motor 507. Thus, while the subject matter is described herein in the context of discrete switching arrangements 513, 515 that enable or otherwise provide a path for input power to the motor 507 from the energy source 503, in practice, discrete switching arrangements 513, 515 may not be present in an embodiment of the infusion device 502. For example, the functionality of the switching arrangements 513, 515 may be integrated into a motor driver module 514 which includes enable/disable functionality associated with its input and output, in which case, the pump control module 520 will be coupled to the motor driver module 514 to control the status (e.g., enabled or disabled) of the input power to the motor driver module 514, while the motor control module 512 coupled to the motor driver module 514 to control the status (e.g., enabled or disabled) of the output power from the motor driver module 514.

Figure 6:
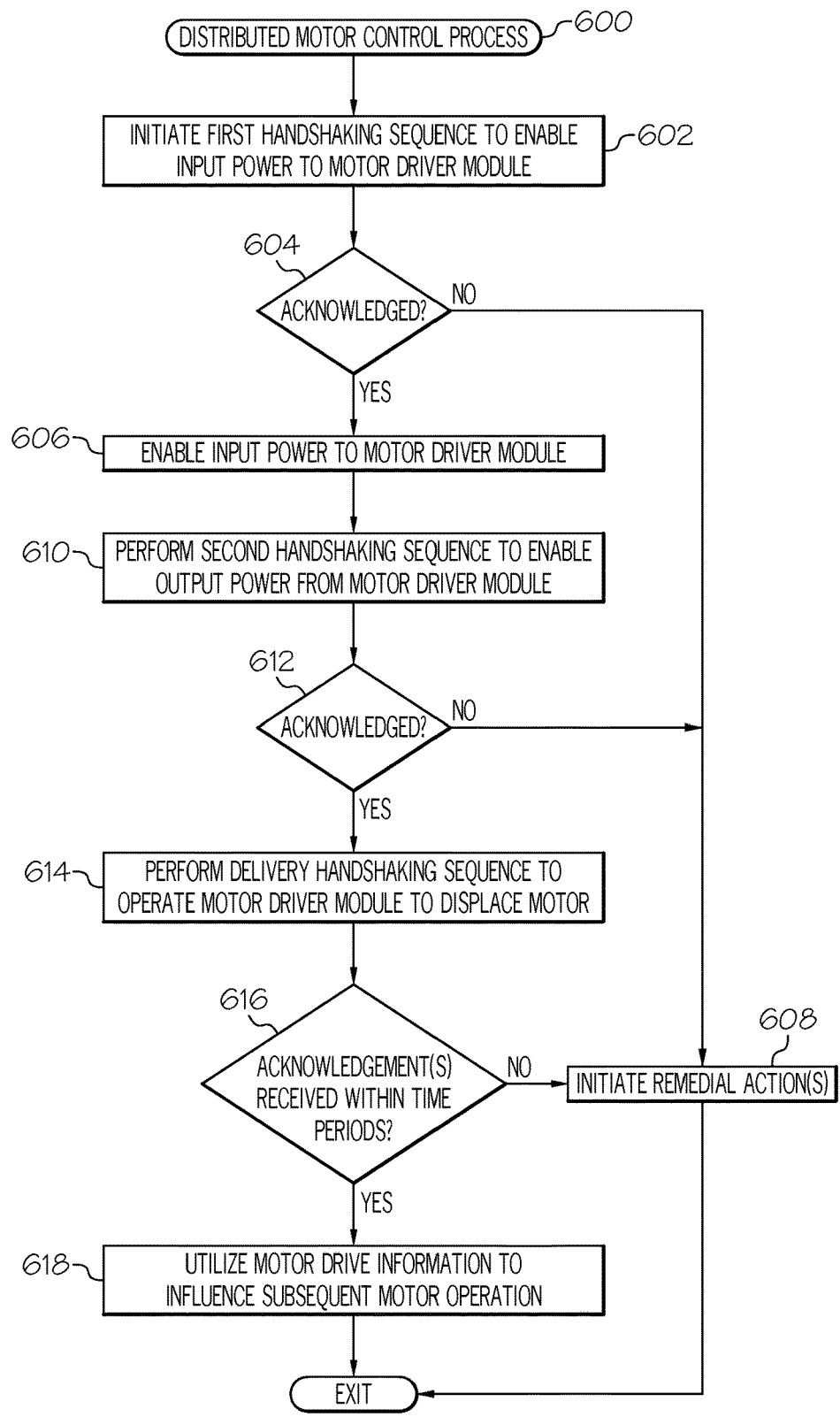
FIG. 6 is a flow diagram of an exemplary distributed motor control process suitable for use with the control system of FIG. 5.

FIG. 6 depicts an exemplary distributed motor control process 600 suitable for implementation by the control modules 512, 520 of the control system 500 associated with the fluid infusion device 502 to safely operate the motor 507 in accordance with a handshaking sequence of communications. For purposes of explanation, the distributed motor control process 600 may be described herein in the context of a closed-loop operating mode, however, it will be appreciated that the subject matter described herein is not limited to the particular operating mode being implemented. Various tasks performed in connection with the distributed motor control process 600 may be performed by hardware, firmware, software executed by processing circuitry, or any combination thereof. For illustrative purposes, the following description refers to elements mentioned above in connection with FIGS. 1-5. In practice, portions of the distributed motor control process 600 may be performed by different elements of the control system 500, such as, for example, the pump control module 520, the motor control module 512, the energy source 503, the switching arrangements 513, 515, the motor driver module 514, the rotor sensing arrangement 516 and/or the user interface element(s) 540. It should be appreciated that the distributed motor control process 600 may include any number of additional or alternative tasks, the tasks need not be performed in the illustrated order and/or the tasks may be performed concurrently, and/or the distributed motor control process 600 may be incorporated into a more comprehensive procedure or process having additional functionality not described in detail herein. Moreover, one or more of the tasks shown and described in the context of FIG. 6 could be omitted from a practical embodiment of the distributed motor control process 600 as long as the intended overall functionality remains intact.

The distributed motor control process 600 provides handshaking sequences of communications between control modules of an infusion device that are to be performed whenever a motor of an infusion device is to be operated to deliver fluid to the body of a patient (e.g., the user associated with the infusion device). The control of the motor is distributed across different control modules of the infusion device in a manner that facilitates relatively early intervention to ensure an anomalous condition with respect to any one of the control modules does not result in erroneous delivery of fluid to the patient. In this regard, any one of the control modules can unilaterally initiate one or more remedial actions to stop or otherwise prevent further delivery of fluid in response to a deviation from the current handshaking sequence. In exemplary embodiments, the control module that detects an unacceptable deviation from the handshaking sequence prevents subsequent application of electrical power to the motor to thereby prevent further delivery of fluid. Additionally, the control module preventing operation of the motor can also generate or otherwise provide one or more notifications or alerts via an output user interface element associated with the infusion device, thereby notifying the patient or other user of the potential anomalous condition of the infusion device.

The illustrated process 600 begins by performing a first setup handshaking sequence between control modules of the infusion device to enable input power to the motor driver from the infusion device energy source. In response to identifying or otherwise determining that the infusion device should be operated to deliver fluid to the body of a patient, a first control module of the infusion device automatically initiates the initial setup handshaking sequence with another control module of the infusion device prior to enabling the input of electrical power from the energy source to the motor driver module in response to a valid response in accordance with the initial setup handshaking sequence (tasks 602, 604, 606). In this regard, when a valid acknowledgement or response prescribed by the handshaking sequence is not received, one or more remedial actions are automatically initiated to prevent operation of the motor and/or notify the user of a potential anomalous condition (task 608).

Referring to FIG. 5, in exemplary embodiments, the pump control module 520 automatically initiates the initial setup handshaking sequence with the motor control module 512 by transmitting or otherwise communicating a delivery request to the motor control module 512. Thereafter, in response to receiving, from the motor control module 512, an affirmative acknowledgment that the motor control module 512 is capable of operating motor 507 and that input power to the motor driver module 514 can be enabled, the pump control module 520 automatically enables input power to the motor driver module 514, for example, by closing, turning on, or otherwise activating the switching arrangement 513 to provide a path for electrical power output by the energy source 503 to the appropriate input(s) of the motor driver module 514. Conversely, in response to a failure to receive an affirmative acknowledgment from the motor control module 512 within a specified timeout period associated with the delivery request prescribed by the initial setup handshaking sequence, the pump control module 520 maintains the configuration of the switching arrangement 513 in the disconnected, deactivated, or off state to prevent electrical power output by the energy source 503 from being provided to the motor driver module 514. Additionally, in exemplary embodiments, the pump control module 520 also generates or otherwise provides a user notification via a user interface element 540 to indicate, to the patient or other user, a potential anomalous condition with respect to the motor control module 512 and/or the infusion device 502 that may require maintenance or other manual attention.

In one or more exemplary embodiments, prior to providing an affirmative acknowledgment to the pump control module 520, the motor control module 512 may perform one or more diagnostics tests or checks (e.g., self-diagnostics or with respect to one or more of the motor 507, the motor driver module 514, and/or the rotor sensing arrangement 516) to verify or otherwise confirm that the motor control module 512 is capable of operating the motor 507 to achieve a desired amount of delivery of fluid to the user. In such embodiments, based on the outcome of the diagnostic(s) that are performed, the motor control module 512 may provide an indication (or negative acknowledgment) to initiate one or more remedial actions when the motor control module 512 is not capable of operating the motor 507 to achieve a desired amount of delivery of fluid to the user. It should be noted that in situations where the motor control module 512 is malfunctioning, nonresponsive, or inoperable, or when communications between the motor control module 512 and the pump control module 520 are interrupted, the pump control module 520 will not receive an affirmative acknowledgment of the delivery request from the motor control module 512.

Referring again to FIG. 6, and with continued reference to FIG. 5, when the initial setup handshaking sequence is successfully performed, the illustrated control process 600 continues by performing a second setup handshaking sequence between control modules prior to enabling output power from the motor driver to the motor (tasks 610, 612). As described above, the distributed motor control process 600 also automatically initiates one or more remedial actions in response to the absence of a valid acknowledgment or other communication prescribed by the second setup handshaking sequence (task 608). In one or more embodiments, the pump control module 520 automatically initiates the second setup handshaking sequence with the motor control module 512 by transmitting or otherwise communicating an authorization to enable output power from the motor driver module 514 in response to receiving an affirmative acknowledgment of the initial delivery request from the motor control module 512. In such embodiments, the motor control module 512 responds to the authorization message by automatically operating the switching arrangement 515 associated with the output of the motor driver module 514 to electrically connect the output(s) of the motor driver module 514 to the stator winding(s) (or input(s)) of the motor 507. Additionally, in response to successfully operating the switching arrangement 515 to enable output power from the motor driver module 514, the motor control module 512 transmits or otherwise communicates an affirmative acknowledgment responsive to the authorization message that indicates the motor driver output power has been enabled. As described above, if the motor control module 512 is malfunctioning, inoperable, nonresponsive, or the like, the pump control module 520 will not receive an affirmative acknowledgment of the authorization message from the motor control module 512. Thus, after a timeout period associated with the second setup handshaking sequence has elapsed, the pump control module 520 may automatically initiate one or more remedial actions, such as, for example, operating the switching arrangement 513 to disable input power to the motor driver module 514 and generating a user notification via a user interface element 540.

In another embodiment, the second setup handshaking sequence is automatically initiated by the motor control module 512 in response to the initial delivery request received from the pump control module 520. For example, the affirmative acknowledgment provided by the motor control module 512 in response to the initial delivery request may also function as an authorization request for enabling the output power from the motor driver module 514. In such embodiments, if the pump control module 520 is malfunctioning, inoperable, nonresponsive, or the like, the motor control module 512 will not receive the authorization from the pump control module 520, and therefore, will not enable the output power from the motor driver module 514. In this regard, if a timeout period associated with the second setup handshaking sequence elapses, the motor control module 512 may automatically initiate one or more remedial actions (e.g., task 608), such as, for example, maintaining the switching arrangement 515 configured to prevent output power from the motor driver module 514 and generating a user notification via a user interface element 540.

Still referring to FIG. 6, after successfully performing setup handshaking sequences to enable a path for receiving output power from the energy source and enable a path for providing input power to the motor, the distributed motor control process 600 continues by performing a delivery handshaking sequence to provide at least a portion of the output power from the energy source to the motor and achieve a desired amount of fluid delivery to the patient (tasks 614, 616). The distributed motor control process 600 operates motor driver module to displace the rotor of the motor, and thereby a plunger within a fluid reservoir, by an amount of displacement that corresponds to a desired dosage (or delivery) command, and maintains the application of power to the motor in accordance with the delivery handshaking sequence. In this regard, the control modules communicate with one another during fluid delivery to ensure the motor is being operated normally and as expected, and in response to failure to receive an expected acknowledgment or other communication prescribed by the delivery handshaking sequence, one or more remedial actions are automatically initiated to prevent inadvertent overdelivery and notify the patient accordingly (task 608).

In exemplary embodiments, delivery handshaking sequence is initiated by pump control module 520 in response to receiving an acknowledgment that output power from the motor driver module 514 to the motor 507 has been enabled by the motor control module 512. As described in greater detail below in the context of FIG. 7, in exemplary embodiments, the delivery handshaking sequence begins with a delivery command message (or dosage command message) that indicates, to the motor control module 512, how the motor 507 should be operated to administer a particular dosage of fluid to the patient. Based on the delivery command message, the motor control module 512 identifies the commanded dosage of fluid to be delivered and automatically converts the commanded dosage into corresponding motor commands configured to produce a displacement of the rotor of the motor 507, which, in turn, will produce a displacement of the plunger 517 that results in the commanded dosage of fluid being dispensed from the reservoir 524. Thereafter, the motor control module 512 automatically operates the motor driver module 514 in accordance with the motor commands to output or otherwise provide a predetermined portion of the input electrical power from the energy source 503 to the stator windings of the motor 507 in a sequence or order that produces the commanded displacement.

After implementing the motor commands corresponding to the commanded dosage, the motor control module 512 automatically transmits or otherwise communicates an active delivery completion message to the pump control module 520 that acknowledges or otherwise indicates, to the pump control module 520, that the delivery command message was received and implemented by the motor control module 512. Additionally, after implementing the delivery motor commands, the motor control module 512 may operate the switching arrangement 515 to disable output power from the motor driver module 514.

The pump control module 520 monitors the duration of time between transmitting the delivery command message and receiving the active delivery completion message, and automatically initiates one or more remedial actions when the elapsed time exceeds an active delivery threshold timeout period associated with the delivery command message. The active delivery threshold timeout period represents an expected maximum amount of time required for the motor control module 512 to receive the delivery command message and implement the commanded delivery. In this regard, the duration of the first threshold timeout period may correlate to the commanded dosage, so that delivery command messages for larger dosages are associated with longer active delivery timeout periods, and conversely, delivery command messages for smaller dosages are associated with shorter active delivery timeout periods. In exemplary embodiments, the pump control module 520 operates the switching arrangement 513 to disable input power to the motor driver module 514 either in response to receiving the active delivery completion message or automatically in response to failing to receive the active delivery completion message within the active delivery threshold timeout period. In this manner, the pump control module 520 redundantly ensures that the motor 507 is electrically disconnected from the energy source 503 to prevent overdelivery in the event that the functionality or communications capability of the motor control module 512 becomes compromised after it has received the delivery command.

In exemplary embodiments, the delivery handshaking sequence also prescribes a total delivery completion message that indicates that the motor 507 has stopped moving. In this regard, in practice, the momentum of the rotor of the motor 507 may cause the rotor to continue to coast in the actuation direction after the motor control module 512 ceases operating the motor driver module 514 to implement the motor commands. Thus, after operating the motor driver module 514 to implement the motor commands and providing the active delivery completion message, the motor control module 512 monitors the displacement of the motor 507 via the rotor sensing arrangement 516 and detects or otherwise identifies when the motor 507 has stopped moving. For example, the motor control module 512 may periodically sample or otherwise obtain the output of the rotor sensing arrangement 516 and detect or otherwise identify that the motor 507 has stopped moving when the output of the rotor sensing arrangement 516 does not change between successive samples. In response to identifying the motor 507 has stopped moving in the actuation direction, the motor control module 512 transmits or otherwise provides a total delivery completion message to the pump control module 520. In a similar manner as described above, the pump control module 520 monitors the duration of time between transmitting the delivery command message and receiving the total delivery completion message, and automatically initiates one or more remedial actions when the elapsed time exceeds a total delivery threshold timeout period associated with the delivery command message. The total delivery threshold timeout period represents an expected maximum total amount of time required for the motor 507 to completely implement the commanded delivery and stop actuating the plunger 517, and, in a similar manner as described above, the duration of the total delivery threshold timeout period may correlate to the commanded dosage amount.

Additionally, in one or more embodiments, the pump control module 520 also monitors the duration of time between receiving the active delivery completion message and receiving the total delivery completion message, and automatically initiates one or more remedial actions when the elapsed time exceeds a coasting threshold timeout period. The coasting threshold timeout period represents an expected maximum amount of time required for the rotor of the motor 507 to stop rotating when input electrical power is no longer being applied. In exemplary embodiments, the pump control module 520 automatically initiates one or more remedial actions either in response to failing to receive the total delivery completion message within the total delivery threshold timeout period after the delivery command message or in response to failing to receive the total delivery completion message within the coasting threshold timeout period after the active delivery completion message. For example, the pump control module 520 may generate or otherwise provide an alert via a user interface element 540 that indicates the motor 507 (or its associated drive system)

may require maintenance because the rotor of the motor 507 does not stop rotating within a tolerable amount of time after input power is removed.

It should be noted that in some embodiments, the delivery handshaking sequence is initiated by the communication sent by the motor control module 512 in response to the enabling the output power from the motor driver module 514. For example, the acknowledgment provided by the motor control module 512 in response to the authorization message may also function as a request for a delivery command for operating the motor driver module 514 and/or motor 507. In such embodiments, the motor control module 512 may instantiate a timer or otherwise monitor a duration of time between transmitting the response to the authorization message and receiving a delivery command message from the pump control module 520. If a prescribed timeout period associated with receiving the delivery command message elapses, the motor control module 512 may automatically operate the switching arrangement 515 to disable or otherwise disconnect the motor driver module 514 from the motor 507 and/or operate a user interface element 540 to generate or otherwise provide a user notification indicating a potential anomalous condition with respect to the pump control module 520. Thus, if the pump control module 520 begins malfunctioning, becomes nonresponsive, or the like after the motor 507 has been electrically connected to the energy source 503, the motor control module 512 may automatically initiate remedial actions to intervene and prevent unintended operation of the motor 507.

Referring to FIG. 6, after the delivery handshaking sequence is completed, exemplary embodiments of the distributed motor control process 600 obtain information pertaining to the operation of the motor when implementing the delivery command and utilizes that motor drive information to influence subsequent operation of the motor (task 618). For example, when implementing a delivery command, the motor control module 512 may store or otherwise maintain information identifying the initial position of the motor 507 (e.g., the initial position of the rotor obtained via the rotor sensing arrangement 516 before implementing the motor commands), the position (or displacement) of the motor 507 after the active delivery is completed (e.g., the position of the rotor obtained via the rotor sensing arrangement 516 after implementing the motor commands), and the final position (or displacement) of the motor 507 after the rotor has stopped moving (e.g., the final position of the rotor obtained via the rotor sensing arrangement 516). Based on the relationship between the amount of displacement of the motor 507 during active delivery (e.g., the difference between the initial rotor position and the rotor position when active delivery is completed) and the amount of displacement of the motor 507 after active delivery (e.g., the amount that the rotor coasted), the motor control module 512 may dynamically update the relationship between the commanded displacement implemented by the motor control module 512 and the actual or measured displacement of the motor 507 when determining subsequent motor commands to better achieve the desired displacement of the motor 507 that produces the commanded dosage.

The motor drive information stored or otherwise maintained by the motor control module 512 may also be transmitted or otherwise communicated to the pump control module 520 in conjunction with the total delivery completion message. In this regard, the pump control module 520 may utilize the motor drive information to adjust or otherwise modify subsequent dosage commands based on the relationship between the delivered dosage of fluid and the commanded dosage. For example, when the total amount of displacement of the motor 507 indicates that the amount of fluid delivered exceeds the commanded dosage, the pump control module 520 may reduce a subsequent dosage command by the difference to compensate for the difference between the preceding commanded dosage and the actual dosage.

Figure 7:
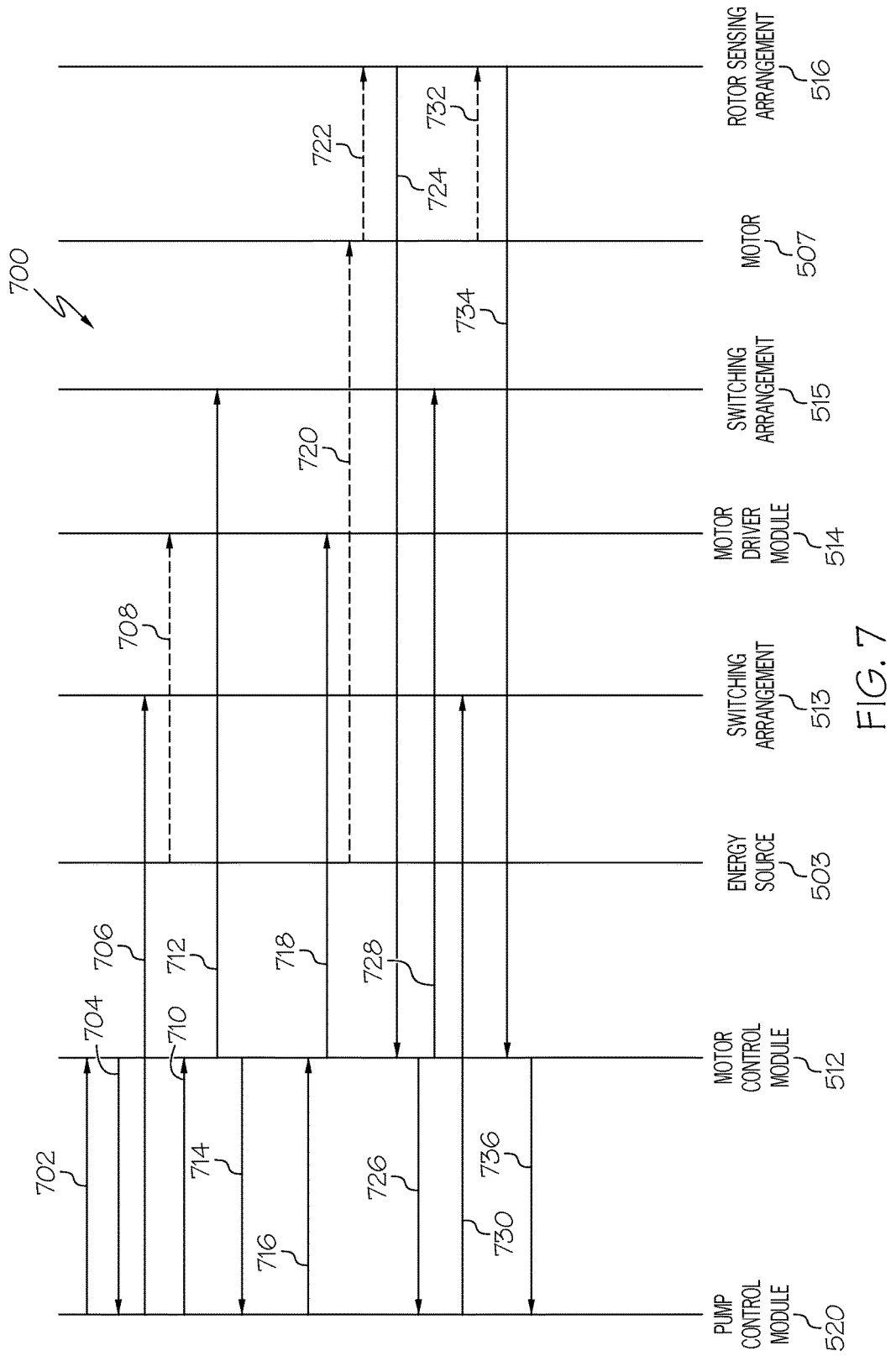
FIG. 7 depicts an exemplary sequence of communications within the control system of FIG. 5 in accordance with one or more embodiments of the distributed motor control process of FIG. 6.

FIG. 7 depicts an exemplary sequence of communications 700 within the control system 500 of FIG. 5 in accordance with an exemplary embodiment of the distributed motor control process 600 of FIG. 6. In exemplary embodiments, the motor 507 is electrically disconnected from the energy source 503 (e.g., by both of the switching arrangements 513, 515 being configured to prevent current flow to the motor 507) when the communications sequence 700 is initiated. In response to determining that the infusion device 502 should be operated to deliver fluid to the body 501 of a patient, the pump control module 520 automatically initiates the initial setup handshaking sequence by transmitting a delivery request message 702 to the motor control module 512. In response to receiving the delivery request message 702, the motor control module 512 may automatically perform one or more diagnostics tests or self-checks to ensure normal operating status before transmitting or otherwise providing an acknowledgment 704 in response to the delivery request message. As described above, if the delivery request acknowledgment 704 is not received by the pump control module 520 within a timeout period associated with the delivery request message 702 and/or the initial handshaking sequence, the pump control module 520 may automatically generate or otherwise provide a user notification indicative of a potential anomalous condition with respect to the motor control module 512.

In response to receiving the acknowledgment 704 of the delivery request message 702, the pump control module 520 operates 706 the switching arrangement 513 to enable electrical power output by energy source 503 being provided 708 to the input(s) of the motor driver module 514. After successfully enabling input power to the motor driver module 514, the pump control module 520 may automatically initiate a second setup handshaking sequence by transmitting or otherwise providing an authorization message 710 to the motor control module 512 that indicates the output power from the motor driver module 514 may be enabled. In response, the motor control module 512 automatically operates 712 the switching arrangement 515 to enable the output power from the motor driver module 514 being provided to the input(s) of the motor 507. After successfully operating the switching arrangement 515 to enable output power from the motor driver module 514, the motor control module 512 transmits or otherwise communicates an acknowledgment 714 in response to the authorization message 710 that indicates the motor driver output power has been enabled. Again, if the driver output power acknowledgment 714 is not received by the pump control module 520 within a timeout period associated with the authorization message 710 and/or the second setup handshaking sequence, the pump control module 520 may automatically generate or otherwise provide a user notification indicative of a potential anomalous condition with respect to the motor control module 512.

After successfully performing the initial setup handshaking sequences to enable or otherwise provide a path for output power from the energy source 503 to the motor 507, the pump control module 520 automatically initiates a delivery handshaking sequence by transmitting or otherwise providing a delivery command message 716 to the motor control module 512 that indicates a commanded dosage to be administered. For example, based on a difference between a glucose measurement value obtained via the sensing arrangement 504 and a target glucose value for the patient, the pump control module 520 may determine an amount of insulin to be delivered to the patient and provide a delivery command message to the motor control module 512 that indicates that determined amount of insulin. The motor control module 512 converts the commanded dosage into corresponding motor commands, and thereafter operates 718 the motor driver module 514 to implement the motor commands and provide 720 at least a portion of the electrical power from the energy source 503 to the motor 507 via the switching arrangements 513, 515 and the motor driver module 514. During operation of the motor 507, the rotor sensing arrangement 516 measures, senses, or otherwise obtains 722 the position or displacement of the rotor of the motor 507, which, in turn, is sampled or otherwise obtained 724 by the motor control module 512. In this regard, the motor control module 512 may provide closed-loop control of the position or displacement of the rotor of the motor 507 based on the measured rotor position to achieve a displacement of the motor 507 that corresponds to the commanded dosage. After operating the motor driver module 514 to implement the motor commands, the motor control module 512 transmits or otherwise provides a message 726 to the pump control module 520 that indicates that active delivery is complete, and additionally, operates 728 the switching arrangement 515 to disable or otherwise disconnect output power from the motor driver module 514 at the motor input.

In response to the active delivery completion message 726, the pump control module 520 automatically operates 730 the switching arrangement 513 to electrically disconnect the motor driver module 514 (and thereby, the motor 507) from the energy source 503. As described above, the pump control module 520 also monitors the duration of time between transmitting the delivery command message 716 and receiving the active delivery completion message 726, and the pump control module 520 automatically operates 730 the switching arrangement 513 to electrically disconnect the energy source 503 if the elapsed time exceeds an active delivery threshold timeout period. Thus, the pump control module 520 redundantly ensures that the motor 507 is electrically disconnected from the energy source 503 to prevent overdelivery in the event that the functionality or communications capability of the motor control module 512 becomes compromised.

As described above, after the motor control module 512 ceases operating the motor driver module 514 to implement the motor commands, the momentum of the rotor of the motor 507 may cause continued displacement of the rotor, which, in turn, is measured or sensed 732 by the rotor sensing arrangement 516. The motor control module 512 continues sampling or otherwise obtaining 734 the output of the rotor sensing arrangement 516 and detects or otherwise identifies when the rotor of the motor 507 has stopped moving. In response to detecting the rotor of the motor 507 has stopped moving in the actuation direction, the motor control module 512 transmits or otherwise provides a total delivery completion message 736 to the pump control module 520. In exemplary embodiments, the total delivery completion message 736 includes motor drive information, which, in turn, may be utilized by the pump control module 520 to adjust or otherwise modify subsequent dosage commands to compensate for differences between the actual amount of fluid that was delivered to the body 501 of the patient relative to the commanded dosage amount.

In exemplary embodiments, the pump control module 520 monitors the duration of time between transmitting the delivery command message 716 and receiving the total delivery completion message 736 and automatically initiates one or more remedial actions when the elapsed time exceeds a total delivery threshold timeout period. Additionally, in one or more embodiments, the pump control module 520 also monitors the duration of time between receiving the active delivery completion message 726 and receiving the total delivery completion message 736, and automatically initiates one or more remedial actions when the elapsed time exceeds a coasting threshold timeout period. In this manner, the pump control module 520 detects or otherwise identifies any potential deterioration or other mechanical anomaly with respect to the motor 507 and/or drive system 208 that allows the rotor of the motor 507 to coast excessively, or alternatively, detects or identifies when the functionality of the motor control module 512 or the communications with the motor control module 512 have become impaired in advance of a subsequent iteration of the distributed motor control process 600. Thus, rather than waiting until a subsequent instance of the communications sequence 700 is initiated, the patient may be notified more immediately that a potential anomalous condition exists with respect to the infusion device 502, which, in turn, allows the patient to undertake remedial actions before the patient requires another dose of fluid.

To briefly summarize, the subject matter describes herein distributes control across control modules (or processors) of the infusion device in a manner that enhances safety by allowing any of the control modules to unilaterally and/or redundantly detect anomalous conditions, stop delivery, and notify the user of potential issues. Each control module may independently implement safety algorithms, diagnostics, or self-checks (e.g., insulin accounting, motor health, software status, or the like), and automatically interrupt delivery and generate alerts whenever it detects an issue. In exemplary embodiments, no control module can enable electrical power to the motor without consent or oversight from another control module in accordance with a handshaking sequence, while any control module can unilaterally disable or remove electrical power from the motor without consent from another control module. Not only can both control modules redundantly remove power from the motor, but the control modules may redundantly generate alerts, which, in turn, reduces the likelihood of an anomalous condition going unaddressed for an extended period of time. Thus, fluid may be safely and accurately delivered while allowing unexpected events or anomalous conditions to be detected and remediated relatively immediately.

For the sake of brevity, conventional techniques related to glucose sensing and/or monitoring, closed-loop glucose control, closed-loop motor control, sensor calibration and/or compensation, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. An infusion device comprising:
   a motor operable to deliver fluid to a body of a user;
   a driver module coupled to the motor;
   a first switching arrangement coupled between the driver module and an energy source;
   a second switching arrangement coupled between the driver module and the motor;
   a first control module coupled to the first switching arrangement; and
   a second control module coupled to the first control module, the driver module, and the second switching arrangement, the first control module operating the first switching arrangement to provide a path for input power from the energy source to the driver module in accordance with a handshaking sequence of communications between the first control module and the second control module and providing a dosage command to the second control module, the second control module operating the second switching arrangement to provide a path for output power from the driver module to the motor in accordance with the handshaking sequence of communications and operating the driver module to deliver the output power comprising a portion of the input power to the motor based at least in part on the dosage command.

2. The infusion device of claim 1, wherein the second control module enables the output power from the driver module to the motor in accordance with the handshaking sequence of communications prior to operating the driver module to deliver the portion of the input power to the motor.

3. The infusion device of claim 1, the handshaking sequence of communications including a first handshaking sequence comprising a delivery request message, the first control module communicating the delivery request message to the second control module, wherein the first control module enables the input power in response to receiving an acknowledgment from the second control module.

4. The infusion device of claim 1, further comprising a user interface element to output a user notification, wherein the first control module is coupled to the user interface element and automatically generates the user notification in accordance with the handshaking sequence of communications in response to an absence of a communication from the second control module within a timeout period prescribed by the handshaking sequence.

5. The infusion device of claim 1, wherein:
   the first control module provides a delivery request, enables the input power to the driver module in response to an acknowledgment of the delivery request, and provides a delivery message comprising the delivery command after enabling the input power; and
   the second control module provides the acknowledgment to the first control module in response to the delivery request and operates the driver module to provide the portion of the input power to the motor based on the delivery message.

6. The infusion device of claim 5, wherein the first control module maintains the input power to the driver module disabled in an absence of the acknowledgement within a timeout period associated with the delivery request.

7. The infusion device of claim 5, further comprising a user interface element to output a user notification, wherein the first control module is coupled to the user interface element and automatically generates the user notification in an absence of the acknowledgement within a timeout period associated with the delivery request.

8. The infusion device of claim 5, the first control module providing an authorization message after enabling the input power and prior to providing the delivery message, wherein the second control module enables the output power from the driver module in response to the authorization message.

9. The infusion device of claim 8, wherein the second control module automatically disables the output power from the driver module in response to an absence of the delivery message from the first control module within a timeout period.

10. The infusion device of claim 5, wherein the first control module automatically disables the input power to the driver module after providing the delivery message in response to an absence of a drive completion message from the second control module within a timeout period associated with the delivery message.

11. An infusion device comprising:
    a motor operable to deliver fluid to a body of a user;
    a first control module; and
    a second control module coupled to the first control module, the first control module enabling input power for the motor in accordance with a handshaking sequence of communications between the first control module and the second control module and providing a dosage command to the second control module, the second control module operating the motor using the input power based at least in part on the dosage command in accordance with the handshaking sequence of communications, wherein the first control module automatically disables the input power in accordance with the handshaking sequence of communications after providing the dosage command to the second control module in response to an absence of a completion message from the second control module within a timeout period associated with the dosage command.

12. A method of operating a motor of an infusion device, the method comprising:
    enabling, by a first control module of the infusion device, input power from an energy source to a driver module coupled between the energy source and the motor in accordance with a first sequence of communications between the first control module and a second control module of the infusion device;

after enabling the input power, enabling, by the second control module, output power from the driver module to the motor in accordance with a second sequence of communications between the first control module and the second control module; and after enabling the output power from the driver module, operating the driver module to provide the input power to the motor in accordance with a third sequence of communications between the first control module and the second control module, wherein operating the driver module in accordance with the third sequence of communications comprises the first control module automatically disabling the input power to the driver module in response to an absence of a drive completion message from the second control module.

13. The method of claim 12, wherein enabling the input power comprises the first control module communicating a request to the second control module and automatically enabling the input power in response to receiving an acknowledgment to the request from the second control module.

14. The method of claim 13, wherein enabling the output power comprises the second control module automatically enabling the output power in response to receiving an authorization message from the first control module after providing the acknowledgment.

15. The method of claim 14, wherein operating the driver module in accordance with the third sequence of communications comprises the second control module automatically disabling the output power in response to an absence of a delivery message from the first control module within a timeout period after communicating the acknowledgment.

16. The method of claim 12, wherein operating the driver module in accordance with the third sequence of communications comprises the first control module communicating a delivery message to the second control module, wherein the second control module operates the driver module in accordance with the delivery message.

17. The method of claim 16, wherein operating the driver module in accordance with the third sequence of communications comprises the first control module automatically disabling the input power after communicating the delivery message in response to the absence of the drive completion message from the second control module within a timeout period associated with the delivery message.

* * * * *